United States Patent
Han et al.

(10) Patent No.: US 8,358,736 B2
(45) Date of Patent: Jan. 22, 2013

(54) APPARATUS, METHOD AND COMPUTER-READABLE MEDIUM ANALYZING COMPONENTS USING X-RAY

(75) Inventors: Seok Min Han, Seongnam-si (KR); Young Hun Sung, Hwaseong-si (KR); Jong Ha Lee, Hwaseong-si (KR); Sung Su Kim, Yongin-si (KR); Dong-Goo Kang, Suwon-si (KR); Kwang Eun Jang, Suyeong-gu (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 133 days.

(21) Appl. No.: 12/926,363

(22) Filed: Nov. 12, 2010

(65) Prior Publication Data

US 2011/0110489 A1    May 12, 2011

(30) Foreign Application Priority Data

Nov. 12, 2009  (KR) ........................ 10-2009-0109001

(51) Int. Cl.
 *G01N 23/06* (2006.01)
(52) U.S. Cl. ........................................................ 378/53
(58) Field of Classification Search ................ 378/51, 378/54, 57, 62, 98.8
 See application file for complete search history.

(56) References Cited

U.S. PATENT DOCUMENTS

| 7,082,185 | B2 * | 7/2006 | Freifeld et al. ................... 378/53 |
| 7,113,566 | B1 | 9/2006 | Peled et al. |
| 7,551,719 | B2 | 6/2009 | Yokhin et al. |
| 2009/0052621 | A1 * | 2/2009 | Walter et al. ..................... 378/53 |
| 2010/0172470 | A1 * | 7/2010 | Kuwabara ........................ 378/53 |

FOREIGN PATENT DOCUMENTS

| JP | 8-327525 | 12/1996 |
| JP | 11-287643 | 10/1999 |
| JP | 2000-97883 | 4/2000 |
| JP | 2000-249532 | 9/2000 |
| JP | 2009-42134 | 2/2009 |

* cited by examiner

*Primary Examiner* — Irakli Kiknadze
(74) *Attorney, Agent, or Firm* — Staas & Halsey LLP

(57) ABSTRACT

Provided is an apparatus, method and computer-readable medium analyzing components using an X-ray. The apparatus, method and computer-readable medium may photograph an object using an X-ray of at least two energy bands to output X-ray images, predict a component ratio of the object using the X-ray images, calculate a length of the object for each of the at least two energy bands using an intensity of the X-ray images, when the object is configured in the predicted component ratio, and verify whether an error in the component ratio occurs by comparing the lengths of the object calculated for each of the at least two energy bands.

18 Claims, 6 Drawing Sheets

APPARATUS, METHOD AND COMPUTER-READABLE MEDIUM ANALYZING COMPONENTS USING X-RAY

CROSS-REFERENCE TO RELATED APPLICATIONS

This application claims the benefit of Korean Patent Application No. 10-2009-0109001, filed on Nov. 12, 2009, in the Korean Intellectual Property Office, the disclosure of which is incorporated herein by reference.

BACKGROUND

1. Field

One or more embodiments relate to an apparatus, a method and a computer-readable medium analyzing components using an X-ray, and more particularly, to an apparatus, a method and a computer-readable medium analyzing components using an X-ray, which may analyze a component ratio of an object by employing X-ray images photographed using the X-ray having various wavelengths and by utilizing a thickness of the object.

2. Description of the Related Art

X-rays may be electromagnetic waves having a relatively short wavelength, and are generated when electrons released by a cathode at a high velocity collide with a heavy metal within a vacuum. X-rays may have high penetrating abilities with respect to objects, and may be changed into visible rays by employing a fluorescent effect.

In addition, X-rays can be photographed, and a part of penetrated X-rays may be absorbed into an object to be attenuated. Thus, changes in density or thickness of the object can be detected by means of photographing with X-rays.

A conventional method of analyzing components of an object by utilizing X-ray images photographed using X-rays having various wavelengths may not separate and analyze similar components included in the object. For example, a human body includes bones, water, and fat, but since the water and the fat have a similar attenuation curve of X-rays, a component ratio of the water and the fat cannot be obtained.

SUMMARY

The foregoing and/or other aspects are achieved by providing an apparatus for analyzing components using an X-ray, the apparatus including: an X-ray photographing unit to photograph an object using an X-ray of at least two energy bands to output X-ray images; a component ratio prediction unit to predict a component ratio of the object using the X-ray images; a length calculation unit to calculate a length of the object for each of the at least two energy bands using an intensity of the X-ray images, when the object is configured in the predicted component ratio; and an error verification unit to verify whether an error in the component ratio occurs by comparing the lengths of the object calculated for each of the at least two energy bands.

The error verification unit may determine, as the component ratio of the object, the predicted component ratio when a difference between the lengths of the object calculated for each of the at least two energy bands is within a predetermined range.

Also, the component ratio prediction unit may repeat the predicting of the component ratio of the object when a difference between the lengths of the object calculated for each of the at least two energy bands is greater than a predetermined range based on the verified result of the error verification unit.

The foregoing and/or other aspects are achieved by providing an apparatus analyzing components using an X-ray, the apparatus including: an X-ray photographing unit to photograph an object using an X-ray of at least one energy band to output X-ray images; a length measurement unit to measure a length of the object; a component ratio prediction unit to predict a component ratio of the object using the X-ray images; a length calculation unit to calculate a length of the object for each of the at least one energy band using an intensity of the X-ray images, when the object is configured in the predicted component ratio; and an error verification unit to verify whether an error in the component ratio occurs by comparing the length of the object calculated for each of the at least one energy band and the length of the object measured by the length measurement unit.

The error verification unit may verify whether the error of the component ratio is greater than a predetermined value by comparing a weighted average length of the object and the measured length of the object. In this instance, the weighted average length of the object may be obtained by applying a weight to the lengths of the object calculated for each of the at least one energy band and by averaging the lengths of the object where the weight is applied.

Also, the error verification unit may determine, as the component ratio of the object, the predicted component ratio when the error in the component ratio does not occur.

Also, the component prediction unit may repeat the predicting of the component ratio of the object when the error in the component ratio occurs based on the verified result of the error verification unit.

Also, the length measurement unit may measure the length of the object through a direct physical measurement, measure the length of the object by verifying a reflected laser of the object using a laser scanner, or measure the length of the object by determining a time during which ultrasonic waves penetrate the object or reflect off the object.

The foregoing and/or other aspects are achieved by providing a method of analyzing components using an X-ray, the method including: photographing an object using an X-ray of at least two energy bands to output X-ray images; predicting, by a processor, a component ratio of the object using the X-ray images; calculating, by the processor, a length of the object for each of the at least two energy bands using an intensity of the X-ray images, when the object is configured in the predicted component ratio; and verifying, by the processor, whether an error in the component ratio occurs by comparing the lengths of the object calculated for each of the at least two energy bands.

The verifying may determine, as the component ratio of the object, the predicted component ratio when a difference between the lengths of the object calculated for each of the at least two energy bands is within a predetermined range.

Also, when a difference between the lengths of the object calculated for each of the at least two energy bands is greater than a predetermined range based on the verifying, the method may further include repeating the predicting of the component ratio of the object.

The foregoing and/or other aspects are achieved by providing a method of analyzing components using an X-ray, the method including: photographing an object using an X-ray of at least one energy band to output X-ray images; measuring, by a processor, a length of the object; predicting a component ratio of the object using the X-ray images; calculating, by the processor, a length of the object for each of the at least one energy band using an intensity of the X-ray images, when the object is configured in the predicted component ratio; and verifying, by the processor, whether an error in the component ratio occurs by comparing the length of the object calculated for each of the at least one energy band and the measured length of the object.

The verifying may verify whether the error of the component ratio is greater than a predetermined value by comparing a weighted average length of the object and the measured length of the object. In this instance, the weighted average length of the object may be obtained by applying a weight to the lengths of the object calculated for each of the at least one energy band and by averaging the lengths of the object where the weight is applied.

Also, the verifying may determine, as the component ratio of the object, the predicted component ratio when the error in the component ratio does not occur.

Also, when the error in the component ratio occurs based on the verifying, the method may further include repeating the predicting of the component ratio of the object.

Also, the measuring may measure the length of the object through a direct physical measurement, measure the length of the object by verifying a reflected laser of the object using a laser scanner, or measure the length of the object using a time during which ultrasonic waves penetrate the object or reflect off the object.

The foregoing and/or other aspects are achieved by providing at least one computer readable medium including computer readable instructions that control at least one processor to implement methods of one or more embodiments.

Additional aspects, features, and/or advantages of exemplary embodiments will be set forth in part in the description which follows and, in part, will be apparent from the description, or may be learned by practice of the disclosure.

BRIEF DESCRIPTION OF THE DRAWINGS

These and/or other aspects and advantages will become apparent and more readily appreciated from the following description of the exemplary embodiments, taken in conjunction with the accompanying drawings of which.

DETAILED DESCRIPTION

Reference will now be made in detail to exemplary embodiments, examples of which are illustrated in the accompanying drawings, wherein like reference numerals refer to like elements throughout. Exemplary embodiments are described below to explain the present disclosure by referring to the figures.

Example embodiments relate to a componential analysis apparatus using an X-ray, method and computer-readable medium thereof, which may analyze a component ratio of an object by employing X-ray images photographed using X-rays having various wavelengths and utilizing a thickness of the object.

Figure 1:
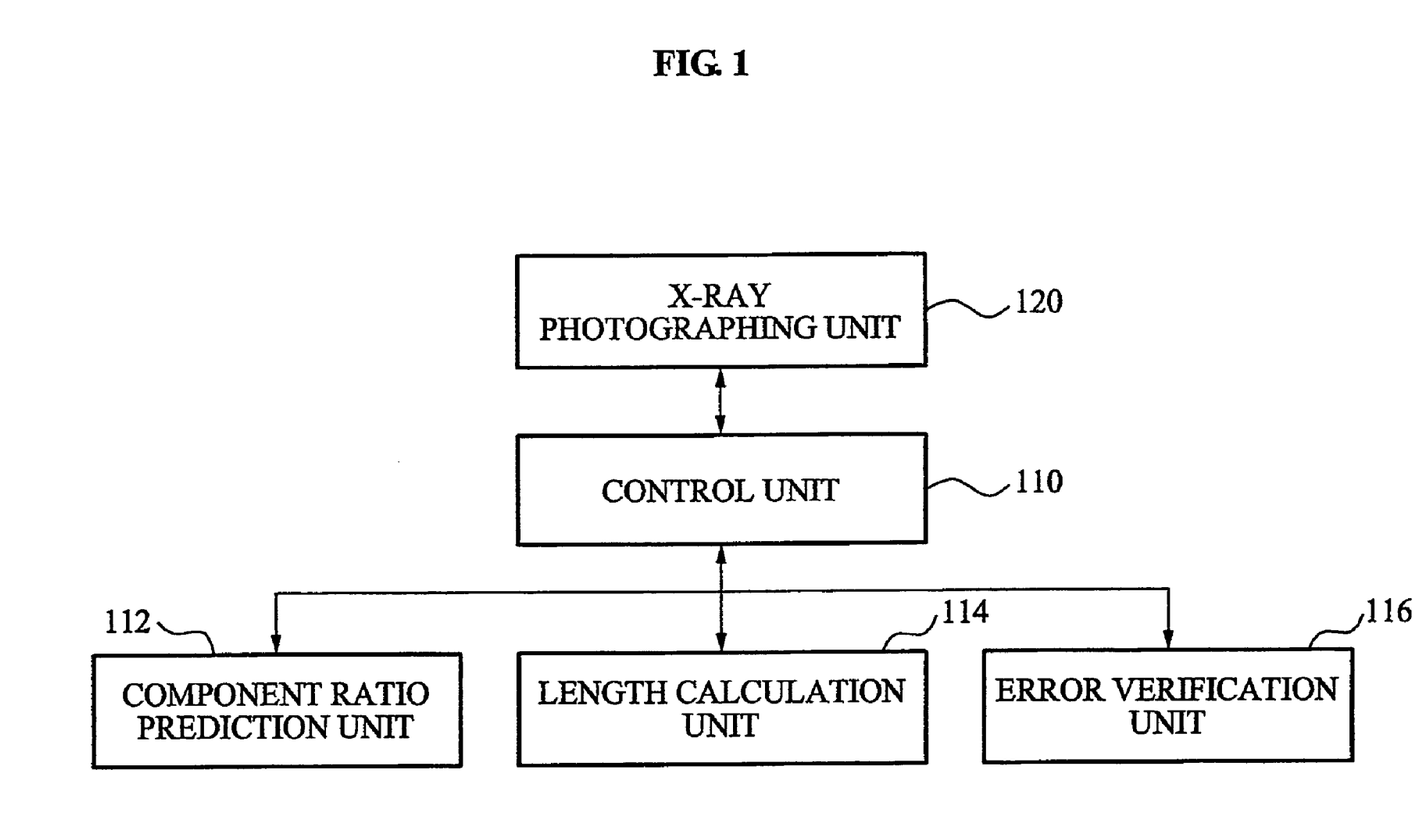
FIG. 1 illustrates a configuration of an apparatus analyzing a component ratio of an object using an X-ray according to example embodiments.

FIG. 1 illustrates a configuration of an apparatus analyzing a component ratio of an object using an X-ray according to example embodiments. Referring to FIG. 1, the apparatus includes a control unit 110, a component ratio prediction unit 112, a length calculation unit 114, an error verification unit 116, and an X-ray photographing unit 120.

The X-ray photographing unit 120 may photograph an object using X-rays of at least two energy bands, and output photographed X-ray images.

The component ratio prediction unit 112 may predict a component ratio of an object using the X-ray images. The component ratio prediction unit 112 may repeatedly predict the component ratio of the object by changing the component ratio of the object until an error is not detected based on a verified result of the error verification unit 116.

The component ratio prediction unit 112 may verify components capable of being separated in the photographed X-ray images to separate the components, and predict an approximated component ratio for components which are difficult to separate. For example, when the object, and target of the component analysis is a human body including bones, water, and fat, the bones may have a high photoelectric effect and a low Compton effect. Conversely, the water and fat may have a low photoelectric effect and a high Compton effect. Accordingly, the bones may be easy to separate, while the water and the fat may be difficult to separate.

The length calculation unit 114 may calculate a length (thickness) of the object for each energy band using various intensities of the X-ray images band when the object is configured in a predicted component ratio.

The error verification unit 116 may verify whether an error in the component ratio occurs by comparing the lengths of the object calculated for each energy band.

When a difference between the lengths of the object calculated for each energy band is greater than a predetermined range, the error verification unit 116 may request that the component prediction unit 112 predicts another component ratio, and when the difference is within the predetermined range, the error verification unit 116 may determine the predicted component ratio as the component ratio of the object.

The control unit 110 may control all operations of the apparatus, and may control the component ratio prediction unit 112, the length calculation unit 114, and the error verification unit 116. Specifically, the control unit 110 may perform functions of the component ratio prediction unit 112, the length calculation unit 114, and the error verification unit 116.

Depending on embodiments, each of the functions, may be separately configured including the component ratio prediction unit 112, the length calculation unit 114, and the error verification unit 116. Accordingly, to practically realize a product, the control unit 110 may be configured to control the component ratio prediction unit 112, the length calculation unit 114, and the error verification unit 116. Alternatively, the control unit 110 may be configured to control at least one of the component ratio prediction unit 112, the length calculation unit 114, and the error verification unit 116.

Figure 2:
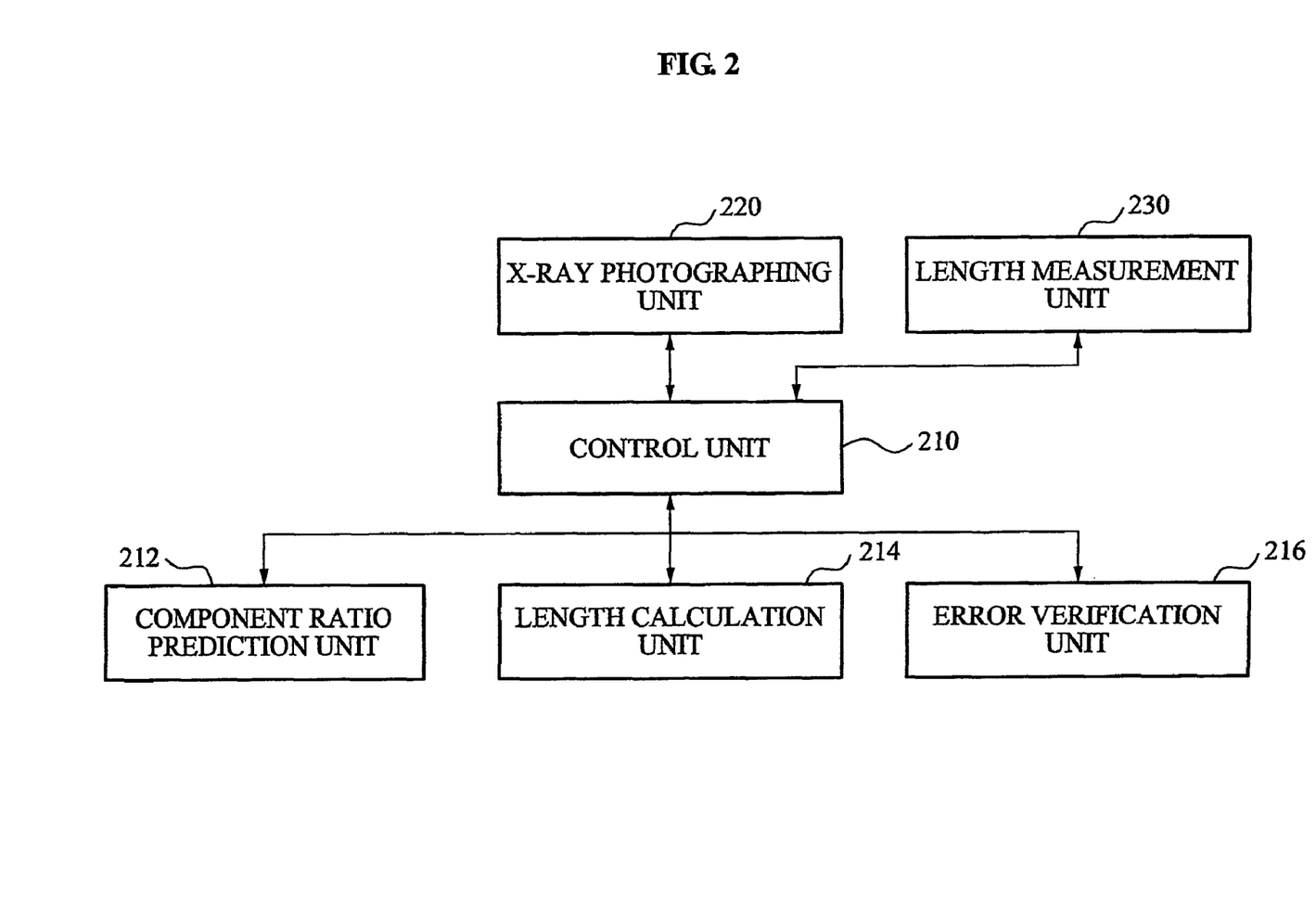
FIG. 2 illustrates a configuration of an apparatus analyzing a component ratio of an object using an X-ray according to example embodiments.

FIG. 2 illustrates a configuration of an apparatus analyzing a component ratio of an object using an X-ray according to example embodiments.

Referring to FIG. 2, the apparatus includes a control unit 210, a component ratio prediction unit 212, a length calculation unit 214, an error verification unit 216, an X-ray photographing unit 220, and a length measurement unit 230.

The X-ray photographing unit 220 may photograph an object using an X-ray having at least one energy band.

The length measurement unit 230 may measure a length of the object. The length measurement unit 230 may measure the length of the object through a direct physical measurement, measure the length of the object by verifying a reflected laser of the object using a laser scanner, or measure the length of the object by determining a time during which ultrasonic waves penetrate the object or reflect off the object. A method of measuring the length of the object will be further described in association with FIGS. 3 and 4.

The component ratio prediction unit 212 may predict the component ratio of the object using the X-ray images. Also, the component ratio prediction unit 212 may repeatedly predict the component ratio of the object by changing the component ratio of the object until the error is not detected based on the verified result of the error verification unit 216.

The component ratio prediction unit 212 may verify components capable of being separated from the photographed X-ray images to thereby separate the components, and predict an approximated component ratio with respect to components which are difficult to separate. For example, when the object, and target of components to be analyzed is a human body including bones, water, and fat, the bones may have a high photoelectric effect, and a low Compton effect. Conversely, the water and fat may have a low photoelectric effect, and a high Compton effect. Accordingly, the bones may be easy to separate, while the water and the fat may be difficult to separate.

The length calculation unit 214 may calculate a length (thickness) of the object for each energy band using intensities of the X-ray images band when the object is configured in a predicted component ratio.

The error verification unit 216 may verify whether an error in the component ratio of the object occurs by comparing the length of the object calculated for each energy band and the length of the object measured in the length measurement unit 230. The error verification unit 216 may verify whether the error of the component ratio is greater than a predetermined value by comparing a weighted average length of the object and the measured length of the object. In this instance, the weighted average length may be obtained by applying a weight to the lengths of the object calculated for each of the at least one energy band and by averaging the lengths of the object where the weight is applied. By applying the weight to the lengths of the object, a specific energy band may allow components of a corresponding object to be easily analyzed.

When a difference between the lengths of the object calculated for each energy band is greater than a predetermined range, the error verification unit 216 may request that the component prediction unit 212 predicts another component ratio, and when the difference is within the predetermined range, the error verification unit 116 may determine the predicted component ratio as the component ratio of the object.

The control unit 210 may control all operations of the apparatus, and may control the component ratio prediction unit 212, the length calculation unit 214, and the error verification unit 216. Specifically, the control unit 210 may perform functions of the component ratio prediction unit 212, the length calculating unit 214, and the error verification unit 216.

Depending on embodiments, each of the functions may be separately configured including the component ratio prediction unit 212, the length calculation unit 214, and the error verification unit 216. Accordingly, to practically embody a product, the control unit 210 may be configured to control the component ratio prediction unit 212, the length calculation unit 214, and the error verification unit 216. Alternatively, the control unit 210 may be configured to control at least one of the component ratio prediction unit 212, the length calculation unit 214, and the error verification unit 216.

Figure 3:
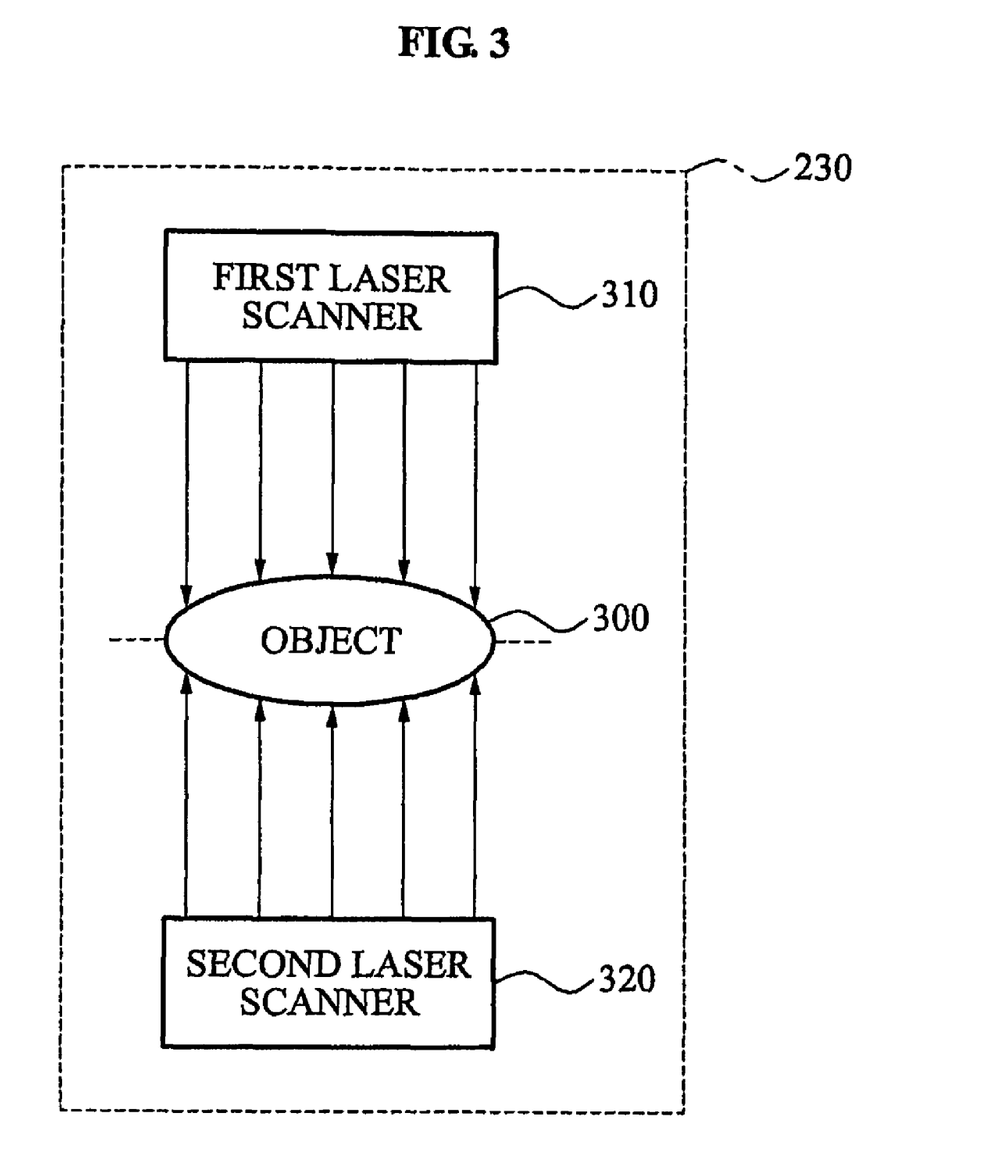
FIG. 3 illustrates a device measuring a length of an object using a laser according to example embodiments.

FIG. 3 illustrates a device measuring a length of an object using a laser according to example embodiments. Referring to FIG. 3, the length measurement unit 230 includes a first laser scanner 310 and a second laser scanner 320. The first and second laser scanners 310 and 320 may project a laser to an object 300, and receive the laser reflected off the object 300 to measure a form of the object.

The object 300 may be interposed by first and second laser scanners 310 and 320 located to face each other. Accordingly, the first and second laser scanners 310 and 320 may each measure a half-form of the object 300, respectively, and a total length of the object 300 may be obtained by combining each measured half-form of the object 300.

Figure 4:
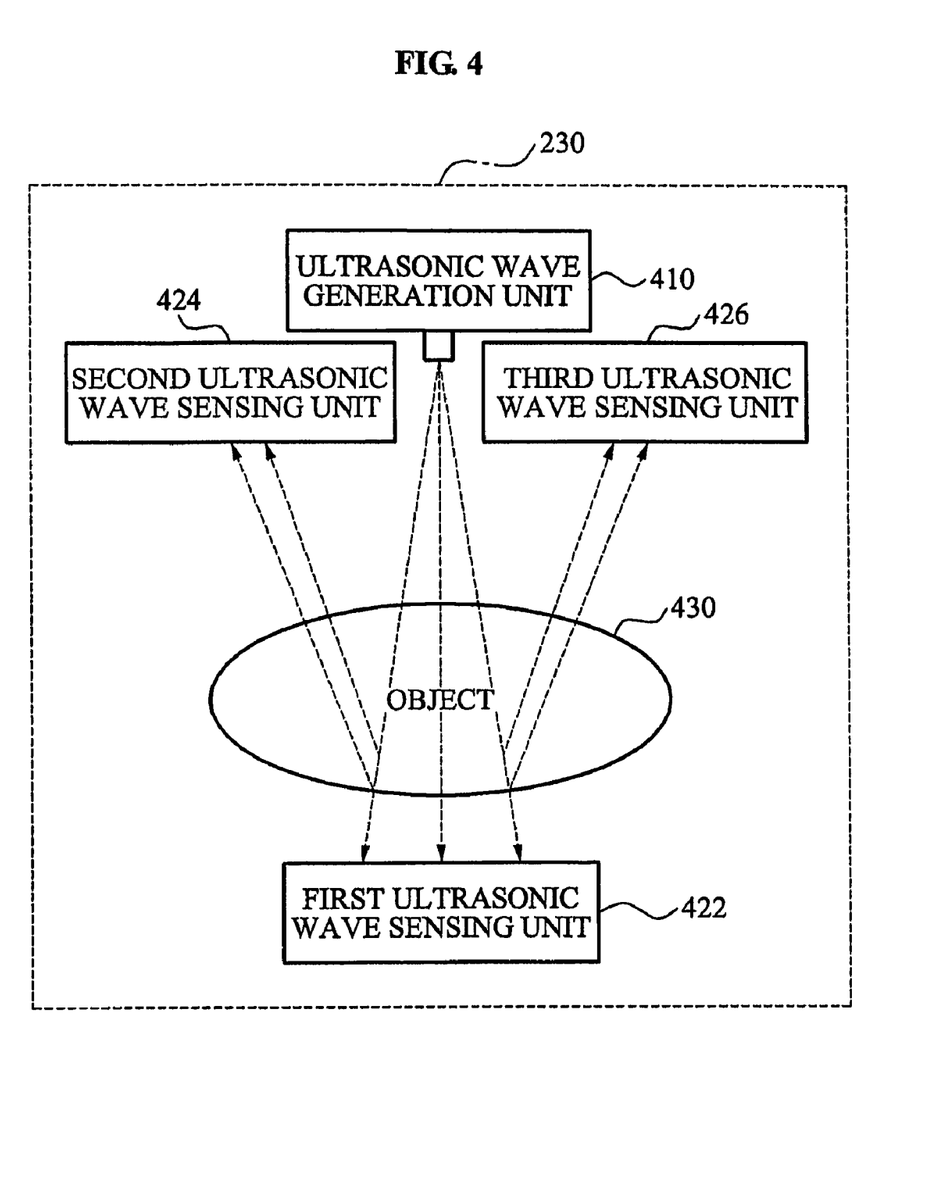
FIG. 4 illustrates a device measuring a length of an object using ultrasonic waves according to example embodiments.

FIG. 4 illustrates a device measuring a length of an object using ultrasonic waves according to example embodiments. Referring to FIG. 4, the length measurement unit 230 may include an ultrasonic wave generation unit 410 and at least one ultrasonic wave sensing unit, for example, first ultrasonic wave sensing unit 422, second ultrasonic wave sending unit 424, and third ultrasonic wave sensing unit 426.

The ultrasonic wave generation unit 410 may project ultrasonic waves to an object 430. Next, the ultrasonic wave sensing units, for example, first ultrasonic wave sensing unit 422, second ultrasonic wave sensing unit 424, and third ultrasonic wave sending unit 426 may measure a length of the object 430 by measuring a time during which ultrasonic waves penetrate the object 430 or reflect off the object 430.

Figure 5:
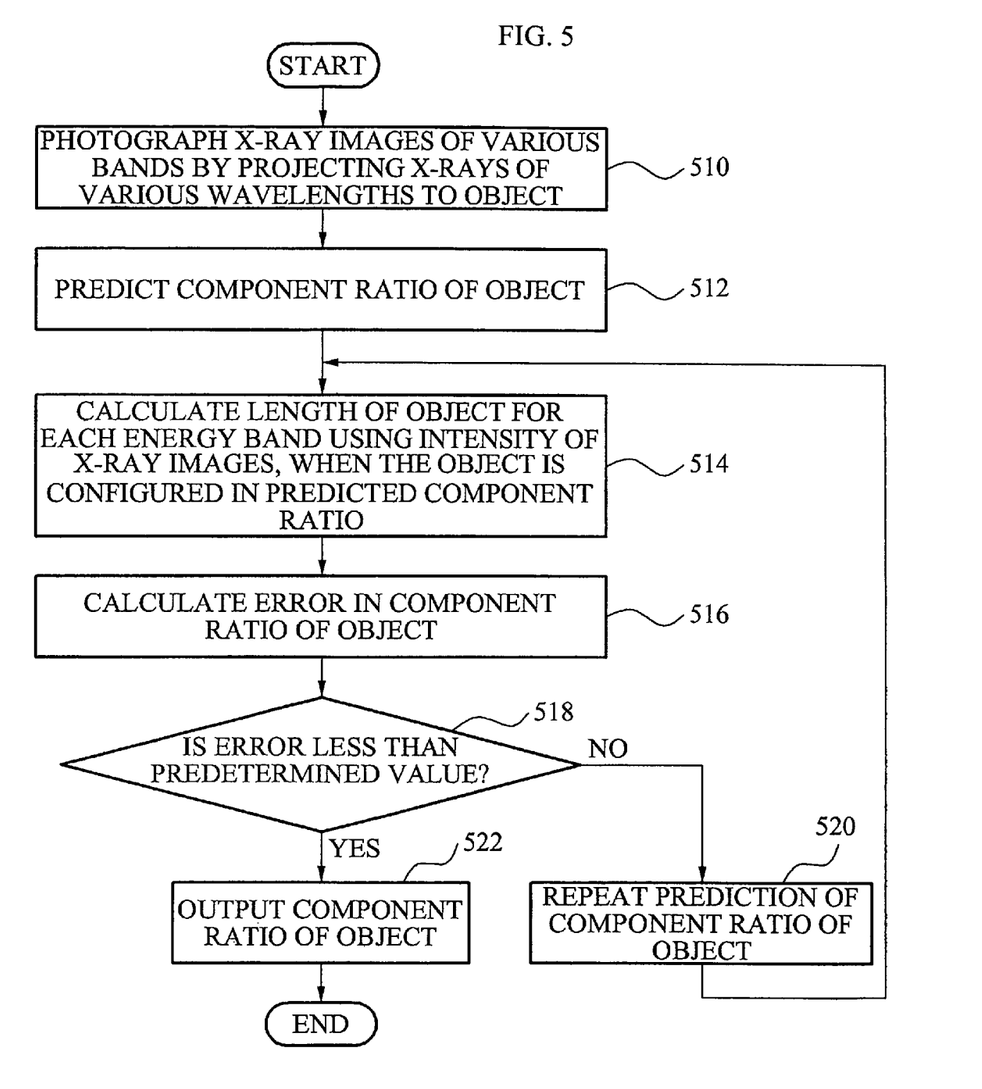
FIG. 5 is a flowchart illustrating a method of analyzing a component ratio of an object using an X-ray according to example embodiments.

Hereinafter, the above described apparatus analyzing the components using X-rays of various wavelengths will be further described with reference to the accompanying drawings. Referring to FIG. 5, in operation 510, when a component ratio of an object is desired to be analyzed, the apparatus may photograph the object using X-rays of a plurality of energy bands to obtain X-ray images. In operation 512, the apparatus may predict the component ratio of the object using the X-ray images.

In operation 514, the apparatus may calculate a length of the object for each energy band using intensity of the X-ray images when the object is configured in a predicted component ratio.

In operation 516, the apparatus may calculate an error in the component ratio by comparing lengths of the object calculated for each energy band. In operation 518, the apparatus may verify whether the error in the component ratio is less than a predetermined value.

In operation 520, when the error is greater than or equal to the predetermined value based on the verified result of operation 518, the apparatus may repeat the prediction of the component ratio of the object, and return to operation 514 to repeatedly perform operations 514 through 518.

In operation 522, when the error is less than the predetermined value based on the verified result of operation 518, the apparatus may output the verified result as the component ratio of the object.

Figure 6:
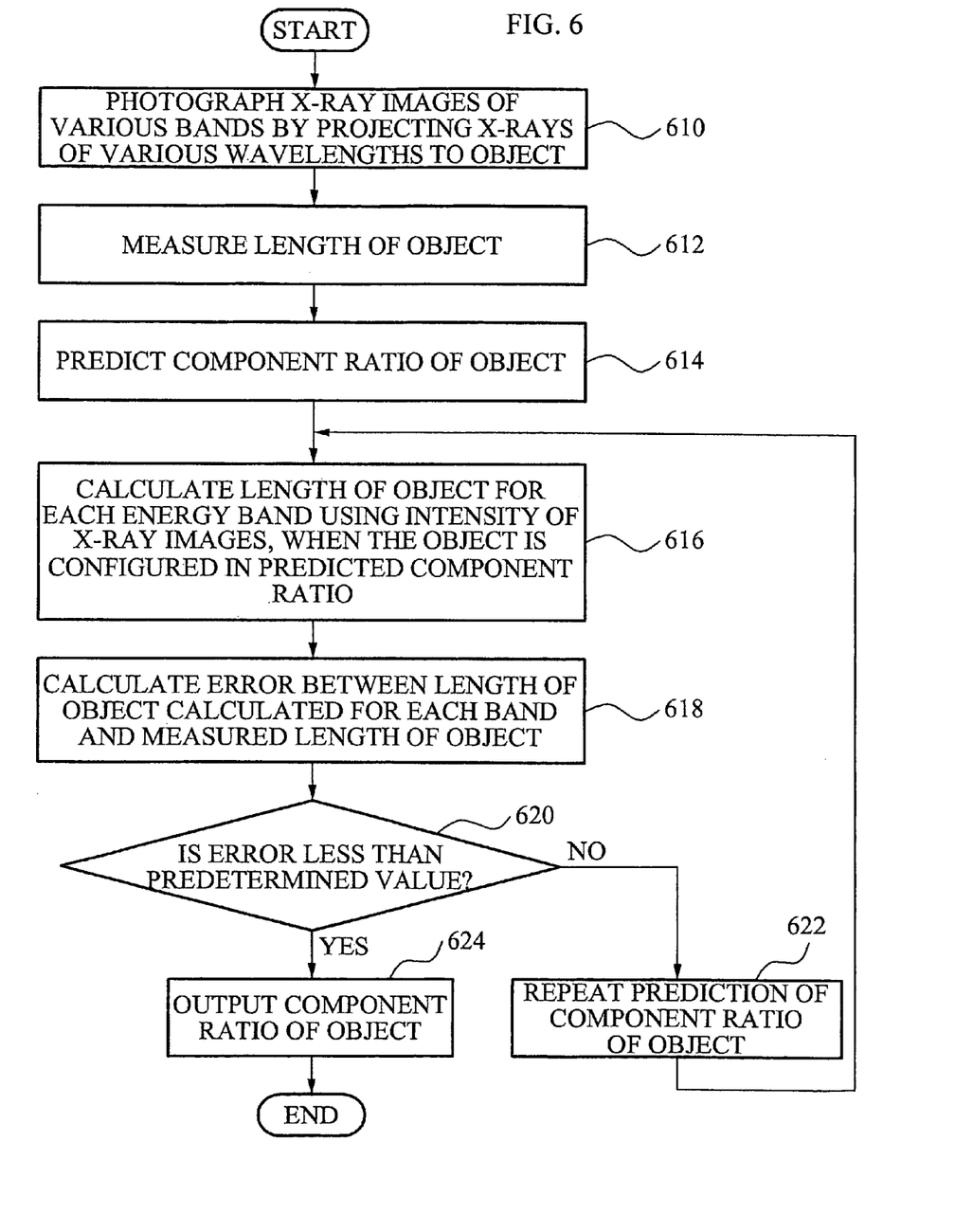
FIG. 6 is a flowchart illustrating a method of analyzing a component ratio of an object using an X-ray according to example embodiments.

FIG. 6 is a flowchart illustrating a method of analyzing a component ratio of an object using an X-ray according to example embodiments. Referring to FIG. 6, in operation 610, when a component ratio of an object is to be analyzed, the component analysis apparatus may photograph the object using X-rays of a plurality of energy bands to obtain X-ray images. In operation 612, the apparatus may measure a length of the object. The apparatus may measure the length of the object through a direct physical measurement, measure the length of the object by verifying a reflected laser of the object using a laser scanner, or measure the length of the object by determining a time during which ultrasonic waves penetrate the object or reflect off the object.

In operation 614, the apparatus may predict the component ratio of the object using the X-ray images. In operation 616, the apparatus may calculate the length of the object for each of the plurality of energy bands, using intensities of the X-ray images, when the object is configured in the predicted component ratio.

In operation 618, the apparatus may calculate an error between the length of the object calculated for each of the plurality of energy bands and the measured length of the object in operation 612. In this instance, the error may be a difference between the length of the object calculated for each of the plurality of energy bands and the measured length of the object. Also, the error may be a difference between a weighted average length of the object and the measured length of the object. In this instance, the weighted average length may be obtained by applying a weight to the lengths of the object calculated for each of the at least one energy band and by averaging the lengths of the object where the weight is applied.

In operation 620, the apparatus may verify whether the error is greater than a predetermined value. In operation 622, when the error is greater than or equal to the predetermined value based on the verified result of operation 620, the apparatus may repeat the prediction of the component ratio and return to operation 614 to thereby perform a series of operations 614 through 618.

In operation 624, when the error is less than the predetermined value based on the verified result of operation 620, the apparatus may output the verified result as the component ratio of the object.

As described above, example embodiments, include the apparatus analyzing the components of the object. The apparatus may analyze a component ratio of the object by employing X-ray images photographed using X-rays having various wavelengths and by utilizing a thickness of the object. Specifically, the apparatus uses characteristics such that a degree in which the X-ray is attenuated varies depending on the energy bands of the X-rays, and the apparatus measures a component ratio of components having similar characteristics from among components constituting the object.

The above described methods may be recorded, stored, or fixed in one or more computer-readable storage media that includes program instructions to be implemented by a computer to cause a processor to execute or perform the program instructions. The media may also include, alone or in combination with the program instructions, data files, data structures, and the like. The media and program instructions may be those specially designed and constructed, or they may be of the kind well-known and available to those having skill in the computer software arts. Examples of computer-readable media include magnetic media such as hard disks, floppy disks, and magnetic tape; optical media such as CD ROM disks and DVDs; magneto-optical media such as optical disks; and hardware devices that are specially configured to store and perform program instructions, such as read-only memory (ROM), random access memory (RAM), flash memory, and the like. The computer-readable media may be a plurality of computer-readable storage devices in a distributed network, so that the program instructions are stored and executed in a distributed fashion. The program instructions may be executed by one or more processors or processing devices. The computer-readable media may also be embodied in at least one application specific integrated circuit (ASIC) or Field Programmable Gate Array (FPGA), which executes (processes like a processor) program instructions. Examples of program instructions include both machine code, such as produced by a compiler, and files containing higher level code that may be executed by the computer using an interpreter. The described hardware devices may be configured to act as one or more software modules in order to perform the operations and methods described above, or vice versa.

Although exemplary embodiments have been shown and described, it should be appreciated by those skilled in the art that changes may be made in these exemplary embodiments without departing from the principles and spirit of the disclosure, the scope of which is defined in the claims and their equivalents.

What is claimed is:

1. An apparatus analyzing components using an X-ray, the apparatus comprising:
    an X-ray photographing unit to photograph an object using an X-ray of at least two energy bands to output X-ray images;
    a component ratio prediction unit to predict a component ratio of the object using the X-ray images;
    a length calculation unit to calculate a length of the object for each of the at least two energy bands based on an intensity of the X-ray images, when the object is configured in the predicted component ratio; and
    an error verification unit to verify whether an error in the component ratio occurs by comparing the lengths of the object calculated for each of the at least two energy bands.

2. The apparatus of claim 1, wherein the error verification unit determines, as the component ratio of the object, the predicted component ratio when a difference between the lengths of the object calculated for each of the at least two energy bands is within a predetermined range.

3. The apparatus of claim 1, wherein the component ratio prediction unit repeats the predicting of the component ratio of the object when a difference between the lengths of the object calculated for each of the at least two energy bands is greater than a predetermined range based on the verified result of the error verification unit.

4. An apparatus analyzing components using an X-ray, the apparatus comprising:
    an X-ray photographing unit to photograph an object using an X-ray of at least one energy band to output X-ray images;
    a length measurement unit to measure a length of the object;
    a component ratio prediction unit to predict a component ratio of the object using the X-ray images;
    a length calculation unit to calculate a length of the object for each of the at least one energy band using an intensity of the X-ray images, when the object is configured in the predicted component ratio; and
    an error verification unit to verify whether an error in the component ratio occurs by comparing the length of the object calculated for each of the at least one energy band and the length of the object measured by the length measurement unit.

5. The apparatus of claim 4, wherein the error verification unit verifies whether the error of the component ratio is greater than a predetermined value by comparing a weighted average length of the object and the measured length of the object, the weighted average length of the object obtained by applying a weight to the lengths of the object calculated for each of the at least one energy band and by averaging the lengths of the object where the weight is applied.

6. The apparatus of claim 4, wherein the error verification unit determines, as the component ratio of the object, the predicted component ratio when the error in the component ratio does not occur.

7. The apparatus of claim 4, wherein the component prediction unit repeats the predicting of the component ratio of the object when the error in the component ratio occurs based on the verified result of the error verification unit.

8. The apparatus of claim 4, wherein the length measurement unit measures the length of the object through one of a direct physical measurement, verifying a reflected laser of the object using a laser scanner, and by determining a time during which ultrasonic waves penetrate the object or reflect off the object.

9. A method of analyzing components using an X-ray, the method comprising:
    photographing an object using an X-ray of at least two energy bands to output X-ray images;
    predicting, by a processor, a component ratio of the object using the X-ray images;
    calculating, by the processor, a length of the object for each of the at least two energy bands using an intensity of the X-ray images, when the object is configured in the predicted component ratio; and
    verifying, by the processor, whether an error in the component ratio occurs by comparing the lengths of the object calculated for each of the at least two energy bands.

10. The method of claim 9, wherein the verifying determines, as the component ratio of the object, the predicted component ratio when a difference between the lengths of the object calculated for each of the at least two energy bands is within a predetermined range.

11. The method of claim 9, wherein, when a difference between the lengths of the object calculated for each of the at least two energy bands is greater than a predetermined range based on the verifying, the method further comprises repeating the predicting of the component ratio of the object.

12. At least one non-transitory computer readable medium comprising computer readable instructions that control at least one processor to implement the method of claim 9.

13. A method of analyzing components using an X-ray, the method comprising:
    photographing an object using an X-ray of at least one energy band to output X-ray images;
    measuring, by a processor, a length of the object;
    predicting, by the processor, a component ratio of the object using the X-ray images;
    calculating, by the processor, a length of the object for each of the at least one energy band using an intensity of the X-ray images, when the object is configured in the predicted component ratio; and
    verifying, by the processor, whether an error in the component ratio occurs by comparing the length of the object calculated for each of the at least one energy band and the measured length of the object.

14. The method of claim 13, wherein the verifying verifies whether the error of the component ratio is greater than a predetermined value by comparing a weighted average length of the object and the measured length of the object, the weighted average length of the object obtained by applying a weight to the lengths of the object calculated for each of the at least one energy band and by averaging the lengths of the object where the weight is applied.

15. The method of claim 13, wherein the verifying determines, as the component ratio of the object, the predicted component ratio when the error in the component ratio does not occur.

16. The method of claim 13, wherein, when the error in the component ratio occurs based on the verifying, the method further comprises:
    repeating the predicting of the component ratio of the object.

17. The method of claim 13, wherein the measuring measures the length of the object through one of a direct physical measurement, verifying a reflected laser of the object using a laser scanner, or determining a time during which ultrasonic waves penetrates the object or reflects off the object.

18. At least one non-transitory computer readable medium comprising computer readable instructions that control at least one processor to implement the method of claim 13.

* * * * *